(12) United States Patent
Bartlett et al.

(10) Patent No.: US 11,281,887 B2
(45) Date of Patent: Mar. 22, 2022

(54) MULTIPLE ELECTRONIC SIGNATURE METHOD

(71) Applicant: Vynca, Inc., Palo Alto, CA (US)

(72) Inventors: Rush L. Bartlett, Mountain View, CA (US); Ashish Kaul, Fremont, CA (US); Ryan J. F. Van Wert, Palo Alto, CA (US); Frank T. Wang, Cupertino, CA (US); Tsung-Wei Wang, Taipei (TW)

(73) Assignee: Vynca, INC., Palo Alto, CA (US)

( * ) Notice: Subject to any disclaimer, the term of this patent is extended or adjusted under 35 U.S.C. 154(b) by 0 days.

(21) Appl. No.: 16/204,399

(22) Filed: Nov. 29, 2018

(65) Prior Publication Data

US 2019/0163957 A1 May 30, 2019

Related U.S. Application Data

(60) Provisional application No. 62/591,936, filed on Nov. 29, 2017.

(51) Int. Cl.
*G06K 9/00* (2006.01)
*G06Q 50/18* (2012.01)
(Continued)

(52) U.S. Cl.
CPC ..... *G06K 9/00181* (2013.01); *G06K 9/00174* (2013.01); *G06K 9/00422* (2013.01);
(Continued)

(58) Field of Classification Search
CPC ........... G06K 9/00181; G06K 9/00442; G06K 9/00422; G06K 9/00174; G06K 9/00161; G06Q 50/188; G06Q 50/167; G16H 10/20
See application file for complete search history.

(56) References Cited

U.S. PATENT DOCUMENTS 6,460,770 B1 10/2002 Kucharczyk
7,542,912 B1 6/2009 Durand
(Continued)

FOREIGN PATENT DOCUMENTS

WO WO 2008084248 7/2008
WO WO 2013093864 6/2013
WO WO2014124014 8/2014

OTHER PUBLICATIONS

SOFTPRO GMBH, "E-Signing on iPad," Retrieved from the Internet URL: https://web.archive.org/web/20120915105226/http://www.softpro.de/data/anonymous_successtories/softpro_insurance_success_story_aia_en.pdf, Retrieved on Jun. 11, 2014 XP055122592, Feb. 1, 2012, 2 pages.
(Continued)

*Primary Examiner* — Ming Y Hon
(74) *Attorney, Agent, or Firm* — Merchant & Gould P.C.

(57) ABSTRACT

A method for enhancing efficiency of a computerized electronic signature system by facilitating collection of signatures from multiple signatories is described. The method may initially involve verifying an identity of a first signatory by receiving data from the first signatory electronically, providing a document to the first signatory, receiving a first electronic signature on the document from the first signatory, and receiving a selection from the first signatory of a second signatory to sign the document as a witness. The method may then involve verifying an identity of the second signatory by receiving data from the second signatory electronically, providing the document to the second signatory, receiving a second electronic signature from the second signatory, providing a completed document, including the first signature and the second signature, and notifying the first signatory and the second signatory that the completed document is completed.

17 Claims, 17 Drawing Sheets

(51) Int. Cl.
    *G06Q 50/16*    (2012.01)
    *G16H 10/20*    (2018.01)
(52) U.S. Cl.
    CPC ....... *G06K 9/00442* (2013.01); *G06Q 50/188* (2013.01); *G06Q 50/167* (2013.01); *G16H 10/20* (2018.01)

(56) References Cited

U.S. PATENT DOCUMENTS

| | | |
|---|---|---|
| 7,620,244 B1 | 11/2009 | Collier |
| 8,306,830 B1 | 11/2012 | Renuart et al. |
| 8,468,610 B2 | 6/2013 | Beals |
| 9,286,482 B1 | 3/2016 | Dumont |
| 9,679,190 B2 | 6/2017 | Bartlett |
| 9,881,201 B2 | 1/2018 | Bartlett |
| 10,032,133 B2 * | 7/2018 | Follis .................... G06Q 10/10 |
| 10,043,056 B1 | 8/2018 | Danyluk et al. |
| 10,425,230 B1 * | 9/2019 | Tang .................... H04L 9/0894 |
| 10,826,997 B2 | 11/2020 | Bartlett, II et al. |
| 2002/0133470 A1 * | 9/2002 | Gruber ............... G06Q 30/0601 705/76 |
| 2003/0140252 A1 | 7/2003 | Lafon et al. |
| 2003/0229515 A1 | 12/2003 | Rizvi |
| 2005/0021376 A1 | 1/2005 | Zaleski |
| 2005/0027544 A1 * | 2/2005 | Newstead ............. G06Q 10/10 705/301 |
| 2005/0102520 A1 * | 5/2005 | Baxter .................... G06F 21/64 713/176 |
| 2005/0132196 A1 | 6/2005 | Dietl |
| 2005/0187794 A1 | 8/2005 | Kimak |
| 2006/0071081 A1 | 4/2006 | Wang |
| 2006/0072144 A1 * | 4/2006 | Dowling ............. H04N 1/4486 358/1.15 |
| 2006/0161973 A1 | 7/2006 | Royer |
| 2006/0184865 A1 * | 8/2006 | Chakraborty .......... G06Q 10/10 715/209 |
| 2006/0287890 A1 | 12/2006 | Stead |
| 2007/0033092 A1 | 2/2007 | Iams |
| 2007/0130084 A1 | 6/2007 | Kay |
| 2007/0188793 A1 | 8/2007 | Wakai |
| 2007/0206248 A1 | 9/2007 | Winterbottom et al. |
| 2008/0072334 A1 * | 3/2008 | Bailey .................... G06Q 10/10 726/28 |
| 2008/0243599 A1 * | 10/2008 | Kwak .................... G07C 13/00 705/12 |
| 2009/0025087 A1 | 1/2009 | Peirson, Jr. et al. |
| 2009/0037224 A1 | 2/2009 | Raduchel |
| 2009/0132351 A1 * | 5/2009 | Gibson ................ G06Q 20/40 705/12 |
| 2009/0164255 A1 | 6/2009 | Menschik et al. |
| 2010/0031140 A1 | 2/2010 | Cummins |
| 2010/0100743 A1 | 4/2010 | Ali et al. |
| 2010/0161993 A1 * | 6/2010 | Mayer ................ H04N 1/32112 713/178 |
| 2010/0217996 A1 * | 8/2010 | Ross ..................... G06Q 20/02 713/179 |
| 2010/0299437 A1 | 11/2010 | Moore |
| 2011/0246230 A1 | 10/2011 | Sie et al. |
| 2011/0271332 A1 | 11/2011 | Jones et al. |
| 2012/0061458 A1 | 3/2012 | Bahr |
| 2012/0284591 A1 * | 11/2012 | Seed .................. G06Q 20/3825 715/201 |
| 2013/0185098 A1 * | 7/2013 | Mitchel .................... G06F 16/93 705/3 |
| 2013/0185210 A1 | 7/2013 | Dodson |
| 2013/0334298 A1 | 12/2013 | Sakpal |
| 2014/0019761 A1 | 1/2014 | Shapiro |
| 2014/0221795 A1 | 8/2014 | Yeager |
| 2014/0275807 A1 | 9/2014 | Redei |
| 2014/0317080 A1 | 10/2014 | Piraino et al. |
| 2015/0010216 A1 | 1/2015 | Papastefanou |
| 2015/0199389 A1 | 7/2015 | Morrison et al. |
| 2015/0213404 A1 * | 7/2015 | Follis ..................... G06F 21/62 705/317 |
| 2015/0242812 A1 | 8/2015 | Nelson |
| 2015/0271179 A1 | 9/2015 | Wang |
| 2015/0294068 A1 * | 10/2015 | Bartlett, II .......... G06F 16/9566 705/51 |
| 2015/0347681 A1 | 12/2015 | Bartlett |
| 2016/0006715 A1 | 1/2016 | Lee |
| 2016/0012556 A1 * | 1/2016 | Moore .................. G06Q 10/10 705/311 |
| 2016/0219027 A1 | 7/2016 | Kaplan |
| 2016/0224962 A1 | 8/2016 | Herwig |
| 2016/0226829 A1 * | 8/2016 | Steeves ................ H04L 63/061 |
| 2016/0232214 A1 * | 8/2016 | Bonda .................. H04L 63/168 |
| 2016/0328523 A1 | 11/2016 | Bartlett |
| 2017/0135142 A1 | 5/2017 | Bartlett |
| 2017/0213069 A1 | 7/2017 | Giron Espon et al. |
| 2018/0053265 A1 * | 2/2018 | Lyon ................... G06F 16/9535 |
| 2018/0089412 A1 | 3/2018 | Kopikare et al. |
| 2018/0139204 A1 * | 5/2018 | Votaw .................... G06F 3/005 |
| 2018/0212782 A1 | 7/2018 | Csik et al. |
| 2018/0247108 A1 | 8/2018 | Hong et al. |
| 2018/0260678 A1 | 9/2018 | Edwards et al. |
| 2018/0270070 A1 * | 9/2018 | Altman ................ G06Q 50/188 |
| 2018/0285838 A1 | 10/2018 | Franaszek et al. |
| 2018/0285983 A1 | 10/2018 | Franaszek et al. |
| 2019/0311021 A1 | 10/2019 | Hayslett et al. |
| 2019/0354706 A1 | 11/2019 | Bartlett |
| 2020/0047865 A1 | 2/2020 | Alsina et al. |
| 2020/0169415 A1 | 5/2020 | Schmidt |
| 2020/0258176 A1 | 8/2020 | Gibson et al. |
| 2020/0403984 A1 | 12/2020 | Minehan |

OTHER PUBLICATIONS

SOFTPRO GMBH, "Samsung GALAXY Note & ATIV PCs: Electronic Signature with SignDoc Mobile," Retrieved from the Internet: URL http://www.slideshare.net/SOFTPROGroup/softpro-signdoc-mobile-app-on-samsung-galaxy-note-electronic-signing, retrieved on Jun. 11, 2014 XP055122653, Apr. 2, 2012, 20 pages.

Trivedi, "Mapping Relational Databases and SQL to MongoDB," https://code.tutsplus.com/articles/mapping-relational-databases-and-sql-to-mongodb-net-35650, Feb. 6, 2014, 15 pages.

Sherman, "Computer-assisted creation of psychiatric advance directives," Community Ment Health J., 34(4):351-362, Aug. 1998.

* cited by examiner

700

PLANNING FOR YOUR CARE

If you were to become suddenly very sick or get into an accident, and were unable to speak for yourself, it is important for your healthcare team to understand your care preferences.

[Healthcare organization] is providing this tool free of charge which will:

- Help you to reflect on your values and what really matters to you in life, and create a written summary
- Name a healthcare agent who could speak for you if you were unable to do so, and create a legally-valid healthcare power of attorney form
- Share both documents with your healthcare team, healthcare agent, and anyone else you think should know.

| Continue |

| I need some time; remind me in a few days. |

DOCUMENT PROGRESS

○ SURROGATE AND ADVANCE DIRECTIVE
(optional)

○ FAMILY, CULTURE AND SUPPORT
(optional)

LIFE-SUSTAINING TREATMENTS
(optional)

○ VALUES

● SUBMIT

Language: English ▾

WHAT MATTERS MOST

LIFE-SUSTAINING TREATMENTS

If you were faced with a serious, life-threatening illness, your care team can provide life support treatments like cardiopulmonary resuscitation (CPR), mechanical ventilation (a respirator) and intensive care (ICU). What best describes your feelings about these kinds of treatments?

○ Try all available treatments to extend my life, and continue them even if there is a small chance of recovering and the treatments are uncomfortable.

○ Try all available treatments to extend my life, but stop them if there is little hope of recovering.

○ I do not want treatments to extend my life; I prefer treatments focused on keeping me comfortable.

○ I don't know.

[ Clear ]    [ Accept and Continue ]

NAME A HEALTHCARE AGENT

A healthcare agent is someone that is legally authorized to speak with you if you were to become very sick and unable to speak for yourself.

A healthcare agent is someone who:

- you trust to make important healthcare decisions for you
- knows you well, and understands what matters to you in life
- can communicate effectively with your family and friends, who may have strong opinions about the care you should receive Do not choose a healthcare agent who:

- Provides healthcare to you, including anyone who owns or operates a healthcare facility where you receive care, or a relative of someone that provides care to you.

On the next screen, we'll ask you to name two individuals who could fulfill this role. The first is your primary healthcare agent; you will also be able to name an alternate agent, in case the primary agent is not able to serve in this capacity in the future.

If you'd like, you can take some time to speak to these individuals in advance. Or, if it's easier, we'll send a text or email to these individuals as a way to start the conversation.

| I need some time; remind me in a few days. | I am ready to name my healthcare agents |

NAME A HEALTHCARE AGENT

First Healthcare Agent

Name

Email

Mobile Phone Number

Personal Message

I need some time; remind me in a few days.

Accept and Continue

FIG. 7D

NAME A HEALTHCARE AGENT

Alternate Healthcare Agent (Optional)

Name

Email

Mobile Phone Number

Personal Message

Accept and Continue

I need some time; remind me in a few days.

REVIEW YOUR HEALTHCARE POWER OF ATTORNEY

My name is: JOHN SMITH  DOB: 12/3/1939

My healthcare agent is: MARY SMITH

My alternate healthcare agent is: ROBERT JONES

I have spoken to my agent and they know my goals and wishes as well as any content from guidance I have written. My agent has full authority to make healthcare decisions on my behalf in accordance with my goals and wishes in the event I am unable to speak for myself. In the event I am unable to communicate my wishes then my agent shall have broad authority to interpret my wishes to others in the medical community including:
1. To request that the medical community not treat me, withdraw care, or decide to conduct certain procedures and tests or not, including surgical procedures. To also decide on my behalf if I should be put on life supporting mechanisms such as ventilation or artificial feeding and hydration or be resuscitated if I am in cardiopulmonary arrest. They have full authority to make these decisions on my behalf even if their decision may result in my death;

| I need some time; remind me in a few days. | Accept and Continue |

FIG. 7F

SIGN AND WITNESS THIS DOCUMENT

My Name Is:

Click to link your smartphone to sign document

You can also sign directly below with your mouse (desktop) or finger pad (tablet)

I need some time; remind me in a few days.

Accept and Continue

NAME TWO WITNESSES THAT WILL ELECTRONICALLY SIGN

CLICK HERE TO SEE WHO CAN BE YOUR WITNESS

Name

Email

Mobile Phone Number

Name

Email

Mobile Phone Number

Go Back

Accept and Notify Witnesses

SHARE THE NEWS AND MAKE YOUR PREFERENCES KNOWN!

Once all signatures have been obtained, we will automatically share this news with anyone you think should know, including your Primary Care Provider Name Email or phone number Name Email or phone number Primary Care Provider Fax Number Go Back Share the news!

FIG. 71

WITNESS SIGNATURE

JOHN SMITH has asked to to digitally witness this document. To begin, your identity will first be verified by a third party service.

Before doing so, confirm you are NOT:

- Appointed as this individual's healthcare agent or back-up agent
- Related to the individual by blood, marriage, domestic partnership, or adoption, nor a spouse of any such person.
- A health care provider, including the owner or operator of a health, long-term care, or other residential or community care facility serving the individual
- An employee of the individual's health care provider
- Financially responsible for the individual's health care
- An employee of the individual's life or health insurance provider
- A creditor of the individual or entitled to any part of the individual's estate under a will or codicil, trust, insurance policy, or by operation of intestate succession laws.
- Entitled to benefit financially in any other way after the individual dies.

| I decline or am not qualified to serve as a witness | I confirm the above. Verify My Identity |

790

FIG. 7J

SIGN THIS DOCUMENT AS WITNESS

Click to review document

My Name Is:

I declare that I personally know the person who signed this document, or I have been provided adequate proof of the person's identity, and that the person signed or acknowledged this Power of Attorney for Health Care in front of me, appearing to be of sound mind and under no duress, fraud, or undue influence.

Click to link your smartphone to sign document

You can also sign directly below with your mouse (desktop) or finger pad (tablet)

Go back

Accept and Continue

MULTIPLE ELECTRONIC SIGNATURE METHOD

CROSS-REFERENCE TO RELATED APPLICATIONS

This application claims the benefit of U.S. Provisional Patent Application No. 62/591,936, filed Nov. 29, 2017, entitled, "MULTIPLE ELECTRONIC SIGNATURE METHOD." The disclosure of this priority application is hereby incorporated by reference in its entirety into the present application.

BACKGROUND

Many traditional documents requiring multiple signatures have been historically difficult to replicate in a digital context. In particular, ensuring all legal requirements to satisfy the process of witnessing signatures, for example for advance directive documents, has been a historical barrier to digitizing such documents.

BRIEF SUMMARY

The present disclosure is directed to methods for facilitating the digital creation of documents requiring multiple signatures, particularly those in which dependencies exist between signatures and signatories, such as signatories who are witnesses to a primary signature. In some embodiments, the methods are directed specifically to advance healthcare directive documents, but the disclosure is not limited to such an application.

In one aspect of a present disclosure, a method is described for enhancing efficiency of a computerized electronic signature system by facilitating collection of signatures from multiple signatories. The method first involves verifying an identity of a first signatory by receiving data from the first signatory electronically, providing a document to the first signatory, receiving a first electronic signature on the document from the first signatory, and receiving a selection from the first signatory of at least a second signatory to sign the document as a witness. The method also involves verifying an identity of the second signatory by receiving data from the second signatory electronically, providing the document to the second signatory, receiving a second electronic signature from the second signatory, and providing a completed document, including the first signature and the second signature. The method may additionally involve notifying the first signatory and the second signatory that the completed document is completed.

In some embodiments, the method may also involve receiving a selection of a third signatory to act as an additional witness. Such embodiments may further involve verifying an identity of the third signatory by receiving data from the third signatory electronically, providing the document to the third signatory, and receiving a third electronic signature from the third signatory.

In some embodiments, the second electronic signature is signed by the second signatory on the document. Alternatively, the second electronic signature may be signed by the second signatory on a separate document, where the completed document includes a combination of the document and the separate document.

The method may optionally also allow the first signatory and the second signatory to create login credentials for accessing the document. Another optional step in the method is to electronically notify the second signatory that he or she has been asked to serve as a witness to signing of the document by the first signatory. Some embodiments may also allow the first signatory and the second signatory to access and download the completed document.

The document may be a healthcare advance directive document, in some embodiments. In such embodiments, the method may also involve providing a questionnaire to the first signatory regarding healthcare preferences and designation of one or more signature witnesses, and receiving responses to the questionnaire from the first signatory, where the document is based at least in part on the responses. In alternative embodiments, the document may be a real estate transaction document or any other suitable document requiring signatures from multiple signatories.

In some embodiments, the method may further include electronically receiving information from the first signatory before providing the document, where the document is based at least in part on the received information. Some embodiments may further involve providing login credentials for the first signatory in a first computer system, receiving login information from the first signatory via the first computer system, and receiving a request from the first signatory to log onto a second computer system, where all other steps in the method are performed by the second computer system. Some embodiments may involve receiving all or a portion of the document from the first signatory. Alternatively, the method may involve receiving all or a portion of the document from a document preparer.

In another aspect of the present disclosure, a method for enhancing efficiency of a computerized electronic signature system by facilitating collection of signatures from multiple signatories may initially involve verifying an identity of a first signatory by receiving data from the first signatory electronically, providing a primary document to the first signatory, receiving a first electronic signature on the primary document from the first signatory, and receiving a selection from the first signatory of at least a second signatory to act as a signature witness. The method may then involve verifying an identity of the second signatory by receiving data from the second signatory electronically, providing the primary document to the second signatory, receiving a second electronic signature from the second signatory, providing a completed document, including the first signature and the second signature, and notifying the first signatory and the second signatory that the completed document is completed.

As mentioned above, in alternative embodiments a third signatory may be designated and verified, and the third signatory may also provide a signature. In alternative embodiments, any number of additional signatories may be included.

In some embodiments, the second electronic signature is signed by the second signatory on the primary document. In alternative embodiments, the second electronic signature is signed by the second signatory on an attestation document, where the completed document includes a combination of the primary document and the attestation document.

These and other aspects and embodiments are described in further detail below, in relation to the attached drawing figures.

BRIEF DESCRIPTION OF THE DRAWINGS

FIGS. 7A-7K depict an exemplary workflow and method for completing a goals of care document for healthcare with signature and witnesses in a fully electronic medium.

DETAILED DESCRIPTION

Figure 1:
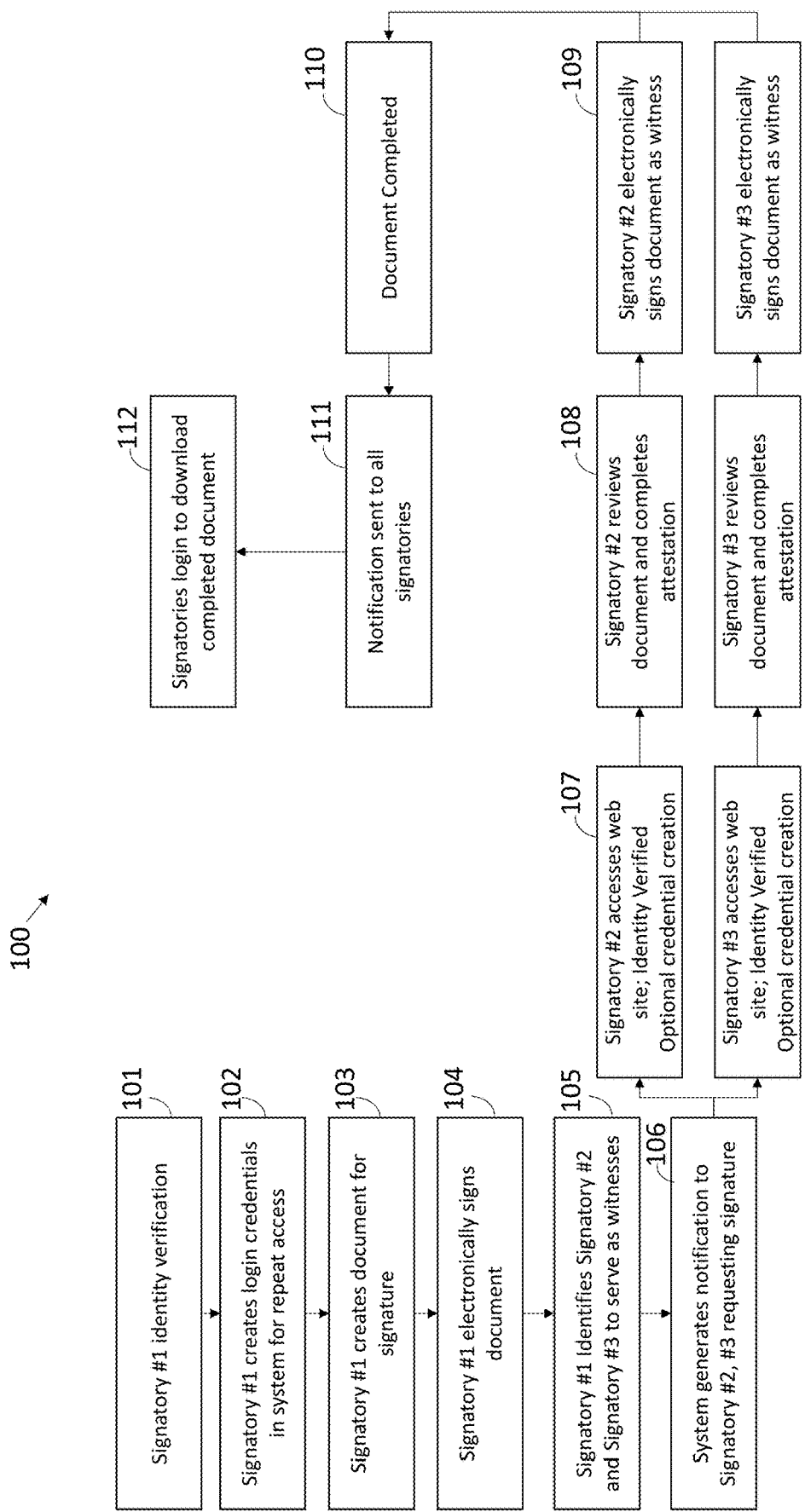
FIG. 1 depicts an exemplary method of completing a document requiring witness signature.

The following description of embodiments should not be interpreted as limiting the scope of the present invention. In alternative embodiments, the methods described herein may include any of a number of additional or alternative features and capabilities. Accordingly, the drawings and descriptions should be regarded as illustrative in nature and not restrictive.

Generally, the method described herein includes: (i) means to review a document; (ii) identity verification of all signatories involved; (iii) collection of a valid electronic signature; and (iv) an attestation by one or more signatories. The process may, in certain embodiments, be facilitated through a web-based system. In this way, the signatories are not required to be in the same physical location, nor are they required to execute the signature at the same time. Rather, the user is simply affirming that any functions, tasks, commitments or other obligations contained in the attestation statement were completed prior to signature.

Various forms of documents may be reviewed, including, but not limited to contracts, advance directive, living wills, healthcare proxy forms, healthcare power of attorney documents, financial power of attorney, wills, and any other document where multiple signatories are required. Documents may be reviewed by some or all of the signatories, depending on the document type.

In various embodiments, identity verification may occur through a variety of means, including, but not limited to, knowledge-based methods, wherein the signatory is challenged with certain question(s) to which only he is aware of the correct response(s), biometric identification, in-person verification of appropriate government-issued or other valid identifying documents, remote verification of appropriate government-issued or other valid identifying documents, or other means of identity verification. Once identity verification has occurred, a signatory may be authenticated through a uniquely assigned username and password or other unique identifying mechanism, such as biometric data like facial recognition, heartbeat, genetic profile, or fingerprints. In some embodiments, one signatory may generate knowledge-based identity verification questions for another signatory, and such questions may be used to perform the identity verification process. These knowledge-based identity verification questions may ask the user questions about her personal history, credit history, or to solve for missing or purposefully corrupted data, such as correcting a digit in a phone number.

The collection of a legally-valid electronic signature is well-described. Such electronic signatures generally comply with legal frameworks describing the requirements for a legally valid electronic signature.

The attestation of the signatory may include a variety of content, depending on the context and purpose of the document to be signed. In the example of a signatory who is serving as a witness to a primary signatory, the attestation statement for the witness would include, for example, that he had confirmed or witnessed the actual signature of the document by the primary signatory. In the case of, for example, advance directives, the attestation may include additional parameters, including but not limited to statements affirming the primary signatory's soundness of mind and lack of duress in signing the document. The attestation statement may or may not also include data from IP address, GPS location, or other confirmatory location based data that could improve the validity of the attestation statement, where the user doing the attestation could include a time and location stamp with their attestation. In addition, the user doing the attestation could include a photo, snapchat, Instagram picture, video, gif, or other digitally captured photographic medium that demonstrates the attesting party is in the same or similar physical location as the original signing party, to confirm the signature witnessing at a physical location and time. In many instances, however, an attestation statement on the part of the witnessing party that they confirm, swear, or hold an oath to the fact that they physically observed the signing party sign the document may be all that is legally required to achieve the act of witnessing.

Embodiments of the electronic signature method described herein include an attestation of viewing or confirming the signing party's signature in a witnessing portion of the method. Embodiments of the method may also include the use of other confirmatory information. The methods described herein are believed to render electronic signature computing technologies more safe and secure while at the same time rendering them more user friendly and accessible to larger numbers of potential users.

FIG. 1 is a flow diagram, illustrating an exemplary method 100, in which a first signatory accesses the system via the web and undergoes an identity verification process 101. After Signatory #1's identity is verified, he or she may optionally create credentials in the system, including but not limited to a username and password 102, to access the system. Signatory #1 creates a document 103 in digital format, reviews it, and signs it electronically 104. Signatory #1 then identifies two signatories (Signatory #2 and Signatory #3), who will serve as witnesses, and enters certain identifying information, for example, a phone number or email 105. The system automatically generates a notification to Signatory #2 and Signatory #3, notifying them of the request to serve as witnesses 106. Signatory #2 and Signatory #3 each independently accesses the system and undergoes identity verification and optionally creation of credentials for later access 107. Signatory #2 and Signatory #3 each independently reviews all, part or none of the document and agrees through click or other means to an attestation statement 108. Once the attestation is completed, Signatory #2 and Signatory #3 electronically sign the document 109. The completed document is then generated 110, and all signatories receive a notification by, for example, email or text message, of the completion of the document 111. Each signatory or other authorized user may then access the document for downloading, printing or transmission by any suitable means, and/or the system may be saved by the system for later viewing 112.

Figure 2C:
FIGS. 2A-C depict exemplary user interfaces for completing a legal advance directive.
Figure 2B:
Figure 2A:
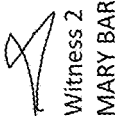

FIGS. 2A-2C show three exemplary user interfaces for the creation of a legal advance directive. FIG. 2A illustrates a care preference selection user interface 200, which the user completing the advance directive uses to make care preference choices in structured or free text format. The top portion 201 of the interface 200 includes preferences with check boxes for the user to check, as appropriate. The middle portion 202 includes a space for the user to select a surrogate decision-maker. The bottom portion 203 of the interface 200 includes spaces for the user to identify the name and contact information of two witnesses for the document. FIG. 2B illustrates a witness attestation interface 210, which may be provided to a witness designated by the user on the user interface 200. The top portion 204 of the attestation interface 210 includes an attestation statement, the middle portion 205 includes a click box the witness can click to agree with the statement, and the bottom portion 206 includes a witness signature line, on which the witness can add a signature.

FIG. 2C shows an exemplary completed advance directive document 212. The completed document 212 includes text 207, at least some of which is based on the preferences entered by the user. Also included are the user's signature 208 and two witnesses' signatures 209. This is but one example, but it illustrates how the method described herein facilitates signing and witnessing of an electronic document by multiple signatories.

Figure 3C:
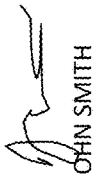
FIGS. 3A-C depict exemplary user interfaces for the completion of a real estate document.
Figure 3B:
Figure 3A:

FIGS. 3A-3C show three exemplary user interfaces for the creation of a real estate transaction. FIG. 3A shows a user input interface 300. The top portion 301 includes an information input area, and the bottom portion includes a witness designation area 302. In alternative embodiments, the information input area may include any of a number of other details for the user to input. In the witness designation area 302, the user may identify the name and contact information for one or two (or more, in some embodiments) witnesses for the document.

FIG. 3B demonstrates an exemplary witness attestation interface 310. The top portion 303 displays a witness attestation statement. The bottom portion 304 includes a blank for the witness to electronically sign. FIG. 3C shows an exemplary completed real estate document 312, including text 305 and signatures 306 of the user and the witnesses. The text may be partially or completely prepopulated with content entered by the user on the user input interface 300.

Figure 4:
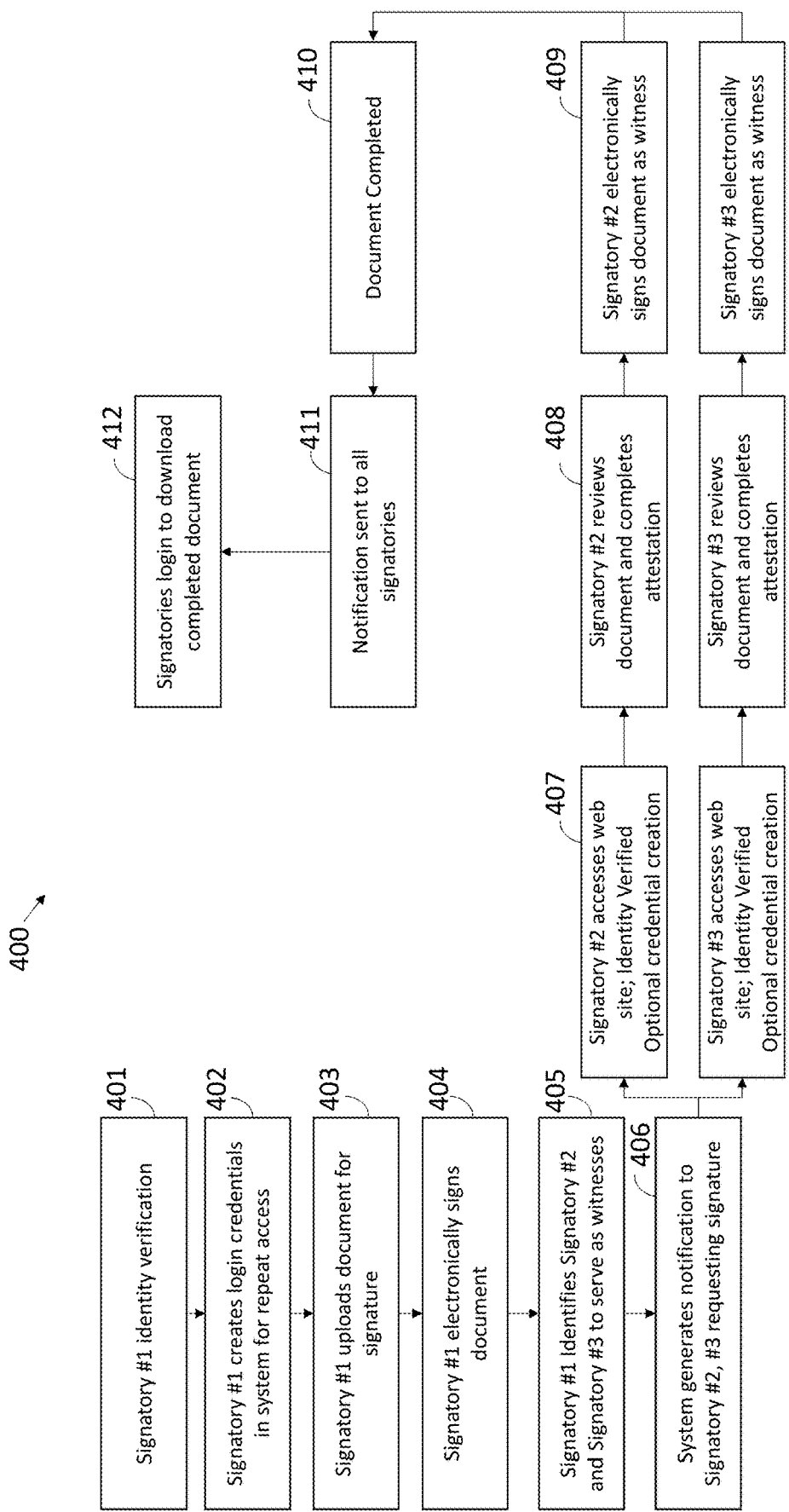
FIG. 4 depicts an exemplary method of signing an uploaded document.

FIG. 4 illustrates an alternative embodiment of an electronic signature attestation method 400. In this embodiment, Signatory #1 accesses the system via the web and undergoes an identity verification process 401. After Signatory #1's identity is verified, Signatory #1 may optionally create credentials in the system, including but not limited to a username and password 402, to access the system. Signatory #1 uploads a document in digital format, using a photo capture or scanning means 403, reviews it, and signs it electronically 404. Signatory #1 then identifies two signatories who will serve as witnesses and enters certain identifying information, such as a phone number or email address 405. The system automatically generates a notification to Signatory #2 and Signatory #3, notifying them of the request to serve as a witness 406. Signatory #2 and Signatory #3 each independently accesses the system and undergoes identity verification and optionally creation of credentials for later access 407. Signatory #2 and Signatory #3 each independently reviews all, part or none of the document and agrees through click or other means to an attestation statement 408. Once the attestation is completed, Signatory #2 and Signatory #3 each electronically signs the document 409. The completed document is then generated 410, and all signatories receive a notification by, for example, email or text message, of the completion of the document 411. Each signatory or other authorized user may then access the document for downloading, printing or transmission by any number of means, and/or the system may be saved by the system for later viewing 412.

Figure 5:
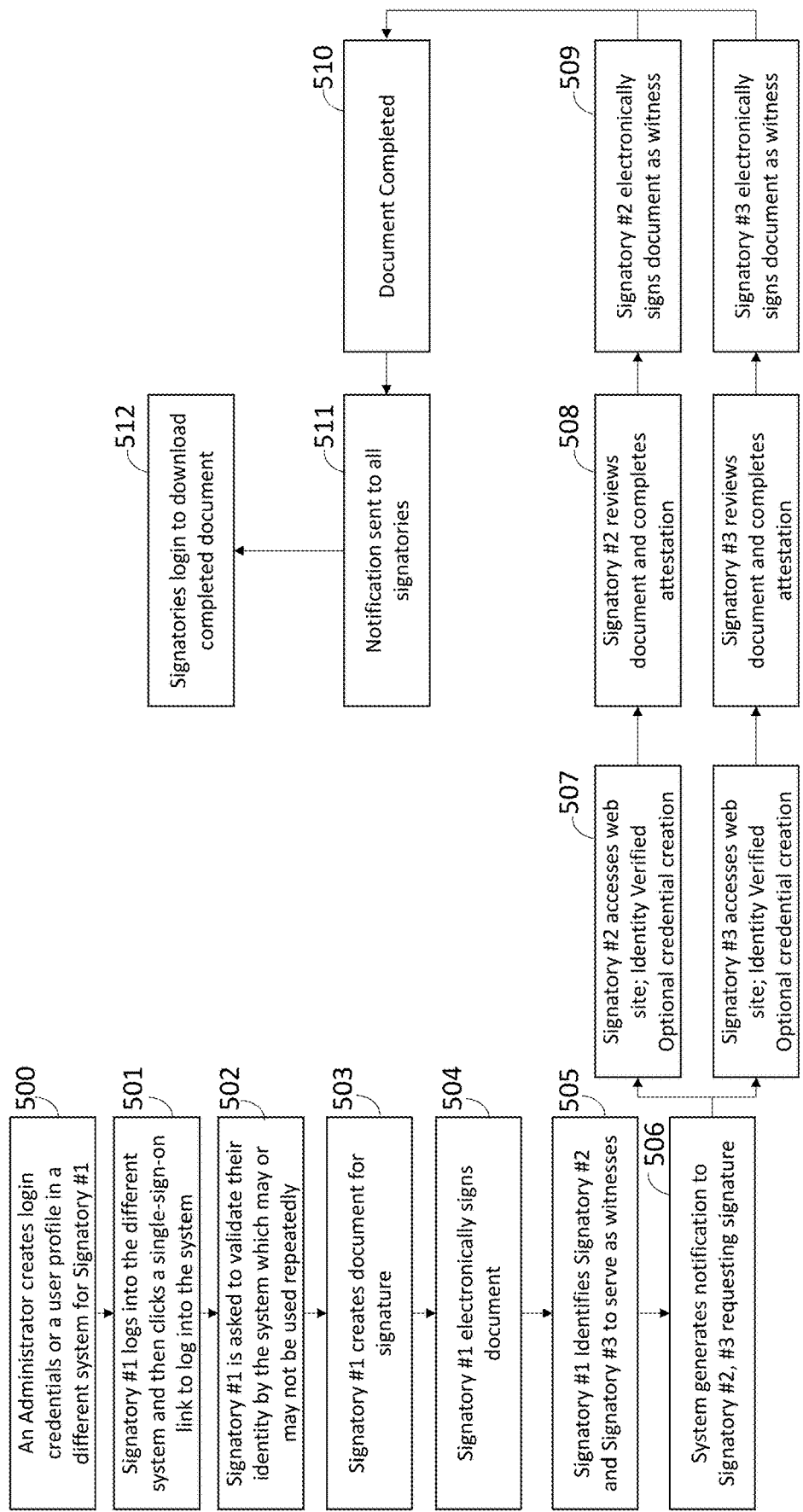
FIG. 5 depicts an exemplary method of completing a document related to witness signature from a system with a single sign-on approach from another system.

FIG. 5 illustrates another embodiment of a method for attesting an electronic document. In this embodiment, a system administrator creates login credentials or a user profile for a signatory in a main system 500, and the account information is used in a single sign-on process to log a user or the signatory into the signatory's profile in the documentation and signature system 501. In the documentation and signature system, Signatory #1 is asked to validate his/her identity independently or as part of a process of another user guiding Signatory #1 through the process 502. Signatory #1 then works to create and/or review a document 503 and signs this document 504. Signatory #1 then identifies two signatories who will serve as witnesses and enters certain identifying information, for example a phone number or email address 505. The system automatically generates a notification to each prospective signatory, notifying them of the request to serve as a witness 506. Signatory #2 and #3 independently access the system and undergo identity verification and optionally creation of credentials for later access 507. Signatory #2 and #3 independently review all, part or none of the document and agree through click or other means to an attestation statement 508. Once the attestation is completed, Signatory #2 and #3 electronically sign the document 509. The completed document is then generated 510, and all signatories receive a notification by, for example, email or text message, of the completion of the document 511. Each signatory or other authorized user may then access the document for downloading, printing or transmission by any number of means, and/or the document may be saved by the system for later viewing 512.

Figure 6:
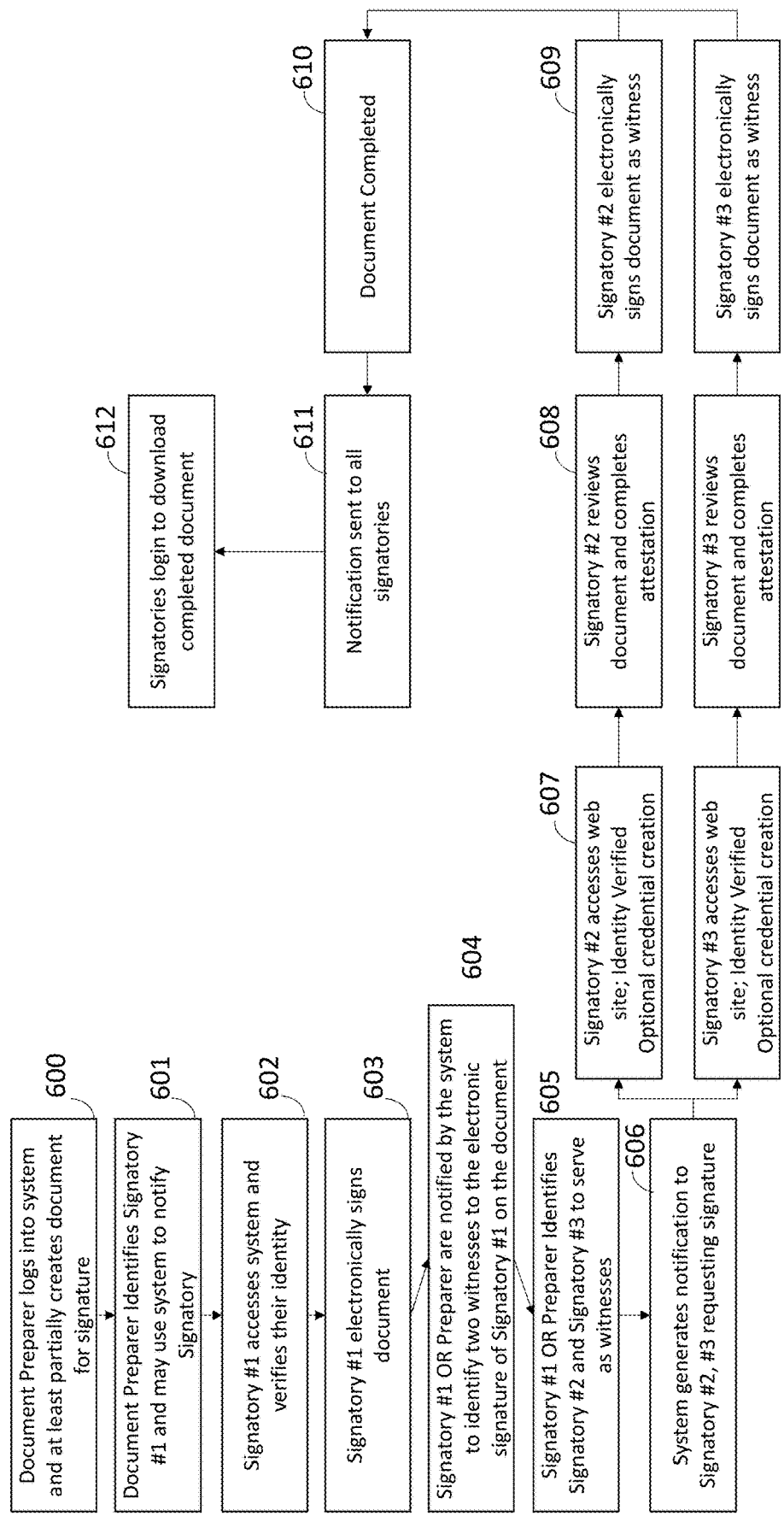
FIG. 6 depicts an exemplary method of completing a document related to witness signature with a document preparer helping to guide the document creation process.

FIG. 6 illustrates yet another alternative embodiment of a method for signing and attesting an electronic document. In this embodiment, a Document Preparer logs into a system to at least partially create a document for signature 600. The Document Preparer identifies a signatory (Signatory #1) before, during, or after the document preparation process, and the system may be used to notify that signatory that the document is requesting their signature 601. Signatory #1 is then asked by the system to verify his/her identity. After Signatory #1's identity is verified, Signatory #1 may optionally create credentials in the system, including but not limited to a username and password to access the system 602. Signatory #1 then may review the document and sign it electronically 603. Then Signatory #1 and/or the Document Preparer are notified by the system that the signature of Signatory #1 has been added to the document and that either Signatory #1 or Document Preparer must identify two witnesses to attest the signature of Signatory #1 on the document 604. Signatory #1 or Document Preparer then identifies two signatories who will serve as witnesses and enters certain identifying information, for example a phone number or email 605. The system automatically generates a notification to each prospective signatory, notifying them of the request to serve as a witness 606. Signatory #2 and #3 independently access the system and undergo identity verification and optionally creation of credentials for later access 607. Signatory #2 and #3 independently review all, part or none of the document and agree through click or other means to an attestation statement 608. Once the attestation is completed, Signatory #2 and #3 electronically sign the document 609. The completed document is then generated 610, and all signatories receive a notification by, for example, email or text message, of the completion of the document 611. Each signatory or other authorized user may then access the document for downloading, printing or transmission by any number of means, and/or the document may be saved by the system for later access 612.

FIGS. 7A-7L depict a series of screenshots and workflows from an exemplary process to complete a declaration of healthcare wishes in the form of a "what matters most note." These healthcare wishes could comprise an advance healthcare directive, living will, power of attorney, or other medical legal order. FIG. 7A is a screenshot of an informational page 700 that provides an overview and informational description that informs the patient that they are able to complete this information now or pass until a later time. The patient's selection can be recorded by the system to trigger follow-up reminders or additional notifications to other accessing members of the system. FIG. 7B is a screenshot of a "what matters most" form 710, which is one of many types of medical/legal documents that could be completed in this workflow to demonstrate the patient's healthcare directives or medical orders by answering a series of questions or writing in responses.

FIG. 7C is a screenshot of a healthcare agent informational page 720, which tells the user he/she will need to designate a healthcare agent for his/her wishes to be valid. This page informs the user about his/her legal rights and who should be named as the healthcare agent/decision maker, based on best practices. FIG. 7D is a screenshot of a healthcare agent designation form 730, which allows the patient to electronically write in the name and contact information of a healthcare agent in order to send them a message to complete the signatory process electronically. FIG. 7E is a screenshot of an alternative healthcare agent designation form 740, indicating a method to send a second alternative healthcare agent information requesting their signature in the signatory process.

FIG. 7F is an exemplary screen shot of a review page 750, demonstrating an attestation that the healthcare agent is known to the patient and that the healthcare agent is informed of the medical wishes for care and the patient agrees to allow that agent to act according to certain described guidelines that are medical and/or legal in nature. FIG. 7G is a screenshot of a sign/witness document 760, which may be provided to the user and the healthcare agent(s) to sign. The document 760 may be signed using a mouse, finger on a touchscreen, any electronic signature method, mobile phone linking method to allow a secondary device like a tablet or smartphone to be used to enter the signature remotely now or later, or the like.

FIG. 7H is a screenshot of a descriptive page 770 that allows the signer to name two witnesses who will electronically sign and attest that they observed the signature process and know it to be true. This ability to name two witnesses includes contact information where the witnesses will be sent links to complete the process. Note that these links could be securely sent or insecurely sent, and if insecurely sent they may require authentication, such as scanning a QR code displayed on the screen or passing a challenge based question set that helps to authenticate the witness identity.

FIG. 7I shows a screenshot of a "share the news" page 780, which allows the user to share his/her wishes with more individuals within the patient's network, including through email, fax, phone, or through social media accounts such as Snapchat, Twitter, Facebook, etc., once the final witness process has been completed. Note that this sharing step can be done by the patient prior to the witness signatures being accepted, and the share notifications can be sent out automatically by the system after the final witness signatures are collected.

FIG. 7J is a screenshot of a witness information page 790, which provides information and legal guidelines for the witness to acknowledge and confirm prior to witnessing the document. FIG. 7K is a screenshot of a witness signature page 800, where the document can be reviewed and the witness enters his/her name and then electronically signs with a noted attestation that they personally know who signed the document and/or they have been given an indication of a person's identity and that they as the witness believe that person appears of sound mind and in no undue influence, duress, or fraud. In addition, the witness may attest that the person signing is physically in front of them at the time of signing, if this is a legal requirement. The electronic signature may take place via any electronic signature mechanism(s), including through primary or secondary devices. The witness may be asked to answer identity based verification questions before and/or after this process of capturing a signature. This witness process can happen one or multiple times if multiple witnesses are required.

We claim:

1. A method for enhancing efficiency of a computerized electronic signature system by facilitating collection of signatures from multiple signatories, the method comprising:

receiving a document associated with estate planning from a first entity, the first entity being a document preparer who prepared the document associated with the estate planning;

verifying an identity of a first signatory by receiving data from the first signatory electronically;

providing the document to the first signatory from the first entity via a first secure link, with the first entity being other than the first signatory;

receiving a first electronic signature on the document from the first signatory;

receiving a selection from the first signatory of at least a second signatory to sign the document as a witness;

verifying an identity of the second signatory by receiving data from the second signatory electronically;

providing the document to the second signatory via a second secure link;

receiving a second electronic signature from the second signatory;

verifying that the first electronic signature and the second electronic signature meet legal requirements for the estate planning;

providing a completed document, including the first signature and the second signature; and notifying the first signatory and the second signatory that the completed document is completed.

2. The method of claim 1, wherein receiving the selection of at least the second signatory further comprises receiving a selection of a third signatory to act as an additional witness, the method further comprising:

verifying an identity of the third signatory by receiving data from the third signatory electronically;

providing the document to the third signatory; and receiving a third electronic signature from the third signatory.

3. The method of claim 1, wherein the second electronic signature is signed by the second signatory on the document.

4. The method of claim 1, wherein the second electronic signature is signed by the second signatory on a separate document, wherein the completed document includes a combination of the document and the separate document.

5. The method of claim 1, further comprising allowing the first signatory and the second signatory to create login credentials for accessing the document.

6. The method of claim 1, further comprising electronically notifying the second signatory that he has been asked to serve as a witness to signing of the document by the first signatory.

7. The method of claim 1, further comprising allowing the first signatory and the second signatory to access and download the completed document.

8. The method of claim 1, wherein the document comprises a healthcare advance directive document.

9. The method of claim 8, further comprising:
providing a questionnaire to the first signatory regarding healthcare preferences and designation of one or more signature witnesses; and
receiving responses to the questionnaire from the first signatory, wherein the document is based at least in part on the responses.

10. The method of claim 1, wherein the document comprises a real estate transaction document.

11. The method of claim 1, further comprising electronically receiving information from the first signatory before providing the document, wherein the document is based at least in part on the received information.

12. The method of claim 1, further comprising:
providing login credentials for the first signatory in a first computer system;
receiving login information from the first signatory via the first computer system; and
receiving a request from the first signatory to log onto a second computer system,
wherein all other steps in the method are performed by the second computer system.

13. The method of claim 1, further comprising receiving all or a portion of the document from the first signatory.

14. A method for enhancing efficiency of a computerized electronic signature system by facilitating collection of signatures from multiple signatories, the method comprising:
receiving a primary document associated with estate planning from a first entity, the first entity being a document preparer who prepared the primary document associated with the estate planning;
verifying an identity of a first signatory by receiving data from the first signatory electronically;
providing the primary document to the first signatory from the first entity via a first secure link, with the first entity being other than the first signatory;
receiving a first electronic signature on the primary document from the first signatory;
receiving a selection from the first signatory of at least a second signatory to act as a signature witness;
verifying an identity of the second signatory by receiving data from the second signatory electronically;
providing the primary document to the second signatory via a second secure link;
receiving a second electronic signature from the second signatory;
verifying that the first electronic signature and the second electronic signature meet legal requirements for the estate planning;
providing a completed document, including the first signature and the second signature; and
notifying the first signatory and the second signatory that the completed document is completed.

15. The method of claim 14, wherein receiving the selection of at least the second signatory further comprises receiving a selection of a third signatory to act as an additional witness, the method further comprising:
verifying an identity of the third signatory by receiving data from the third signatory electronically;
providing the primary document to the third signatory; and
receiving a third electronic signature from the third signatory.

16. The method of claim 14, wherein the second electronic signature is signed by the second signatory on the primary document.

17. The method of claim 14, wherein the second electronic signature is signed by the second signatory on an attestation document, wherein the completed document includes a combination of the primary document and the attestation document.

* * * * *